(12) United States Patent
Holden et al.

(10) Patent No.: US 7,939,270 B2
(45) Date of Patent: May 10, 2011

(54) DELIVERY OF MOLECULES TO A LIPID BILAYER

(75) Inventors: Matthew Alexander Holden, Oxford (GB); John Hagan Pryce Bayley, Oxford (GB)

(73) Assignee: Isis Innovation Limited, Oxford (GB)

( * ) Notice: Subject to any disclaimer, the term of this patent is extended or adjusted under 35 U.S.C. 154(b) by 722 days.

(21) Appl. No.: 11/884,927

(22) PCT Filed: Mar. 22, 2006

(86) PCT No.: PCT/GB2006/001057
§ 371 (c)(1),
(2), (4) Date: Nov. 20, 2007

(87) PCT Pub. No.: WO2006/100484
PCT Pub. Date: Sep. 28, 2006

(65) Prior Publication Data
US 2008/0153150 A1      Jun. 26, 2008

(30) Foreign Application Priority Data
Mar. 23, 2005   (GB) .................................. 0505971.2

(51) Int. Cl.
*G01N 33/53* (2006.01)
(52) U.S. Cl. ........................... 435/7.1; 435/7.2; 436/518
(58) Field of Classification Search .................. None
See application file for complete search history.

(56) References Cited

U.S. PATENT DOCUMENTS

| 3,799,743 A | 3/1974 | Alexander et al. |
| 6,479,288 B1 * | 11/2002 | Laffafian et al. .............. 435/455 |
| 2007/0161101 A1 * | 7/2007 | Takeuchi ................... 435/287.1 |

FOREIGN PATENT DOCUMENTS

| WO | WO 0016101 | * | 3/2000 |
| WO | WO 03/095669 A1 | | 11/2003 |

OTHER PUBLICATIONS

Martin et al. (Langmuir 1998 vol. 14, pp. 3971-3975).*
Laffafian et al, "Lipid-Assistant Microinjection: Introducing Material Into the Cytosol and . . . ", Biophysical Journal, vol. 75, Nov. 1998, 2558-2563; XP-002474002.
Heginbotham et al, "Single Streptomyces lividans K+ Channels Functional Asymmetries and . . . ", J. Gen. Physiol., vol. 114, Oct. 1999, 551-559; XP-002474003.
Mouneimne et al, "Electroinsertion of xeno proteins in red blood cell membranes yields a long lived . . . ", Biochimica et Biophysica Acta. 1066 (1991) 83-89; XP-002977991.
Holden et al, "Direct Introduction of Single Protein Channels and Pores into Lipid Bilayers", J. Am. Chem. Soc., vol. 127, No. 18, 2005, 6502-6503; XP-002474004.

(Continued)

*Primary Examiner* — Jacob Cheu
(74) *Attorney, Agent, or Firm* — Nixon & Vanderhye P.C.

(57) ABSTRACT

A method of delivering a molecule, such as a membrane protein, to a lipid bilayer uses a probe capable of holding the molecule on a carrier surface thereof. The molecule is deposited on the carrier surface and the probe is moved to engage the carrier surface against the lipid bilayer. The carrier surface may be the surface of a drop of hydrogel which adsorbs the molecule. The molecule may be a membrane protein which is thus inserted into the lipid bilayer. The method is fast and simple to perform thereby allowing high throughput experimentation.

30 Claims, 5 Drawing Sheets

OTHER PUBLICATIONS

Bayley et al, "Stochastic sensors inspired by biology", Nature 413, 226-30 (2001).

Holden et al, "Direct Introduction of Single Protein Channels and Pores into Lipid Bilayers", J. Am. Chem. Soc. 127, 6502-6503, Apr. 16, 2005.

Holden et al, "Direct transfer of membrane proteins from bacteria to planar bilayers for rapid screening by single-channel recording", Nature Chemical Biology, 2, 6 (2006), pp. 314-318.

Funakoshi et al, "Lipid Bilayer Formation by Contacting Monolayers in a Microfluidic Device for Membrane Protein Analysis", Anal. Chem. 78(24), 8169-8174, 2006.

White, "The Physical Nature of Planar Bilayer Membranes", Chapter 1 of Ion Channel Reconstitution, C. Miller, Ed., Plenum Press, NY, pp. 3-35 (1986).

Montal et al, "Formation of Bimolecular Membranes from Lipid Monolayers and a Study of Their Electrical Properties", Proc. Nat. Acad. Sci. USA, vol. 69, No. 12, pp. 3561-3566, Dec. 1972.

Google Scholar, http://scholar.google.com/scholar?q=montal+mueller+formation+of=bimolecular&hl= en Dec. 27, 2010.

* cited by examiner

DELIVERY OF MOLECULES TO A LIPID BILAYER

This application is the U.S. national phase of International Application No. PCT/GB2006/001057 filed 22 Mar. 2006 which designated the U.S. and claims priority to 0505971.2 filed 23 Mar. 2005, the entire contents hereby incorporated by reference.

The present invention relates to the delivery to a lipid bilayer of molecules, for example membrane proteins for insertion into the lipid bilayer.

Lipid bilayers having membrane proteins inserted therein constitute membranes in several types of biological system, most notably as cell membranes. Inspired by such natural membranes, a number of technologies have been developed which involve a membrane protein inserted in a lipid bilayer. These technologies require delivery of the membrane protein or another molecule to the lipid bilayer.

One such technology is stochastic sensing in which the response of a membrane protein to a molecule or physical stimulus is used to perform sensing of that molecule or stimulus. The nature of the response depends on the nature of the membrane protein which may be a naturally occurring protein or in many useful applications an engineered protein. In one type of sensing, the membrane protein is a protein pore or a channel which responds to an analyte by affecting an electrical signal developed across the lipid bilayer, for example by changing the ionic current flowing across the lipid bilayer. In this case, sensing of the analyte may be performed by detecting the electrical signal across the lipid bilayer. Stochastic sensing allows sensing of a wide range of biological molecules and systems, for example sensing of ions, organic molecules, or peptides, characterisation of DNA, investigation of ligand-receptor interactions and investigation of multi-step reaction pathways.

Despite the versatility of technology such as stochastic sensing, the practical process is cumbersome, expensive and needs to be performed by a skilled scientist. A significant difficulty lies in the techniques used to insert the membrane proteins into the lipid bilayer for performance of the sensing. The most common technique is to suspend the membrane protein in a purified form into solution and subsequently to wait while the membrane protein diffuses to the lipid bilayer and is inserted by binding to the lipid bilayer and assembling into a functional state. However, in practice the insertion of a single membrane protein into the lipid bilayer can be agonisingly slow and unreliable. In the case of stochastic sensing, it is preferable to have a single pore, as multiple pores prevent or at least complicate kinetic analysis. Low concentrations of the membrane protein in solution are used to prevent multiple pore insertion. Typically the time taken for a membrane protein to be inserted into the lipid bilayer is many minutes or tens of minutes. Apart from being slow and frustrating for the scientist, this is detrimental to any commercial application of the technology.

A related problem occurs with newly engineered proteins. In this case, when there is a lack of activity it is unclear whether this is due to a functional inability of the engineered membrane protein to be inserted into a lipid bilayer, or whether this is due to some other factor such as insufficient concentration, different adsorption properties or simply not having allowed enough time to elapse.

Furthermore, once a single pore has been inserted and monitoring begins, the experiment can be disrupted by the subsequent insertion of another membrane protein from solution into the lipid bilayer. One possible solution to this problem is to perfuse the apparatus to remove excess proteins from solution after insertion of a single pore, but this is a laborious and unreliable step which often results in rupture of the lipid bilayer.

In practical terms, to minimise the time taken for insertion of a membrane protein requires the use of lipid bilayers of relatively large area. However, it would be desirable to reduce the area of the lipid bilayer to lower the electrical noise and to increase stability.

Practical difficulties such as those described above also limit the possibility of applying the membrane proteins in array format as would be desirable for some applications.

It would be desirable to develop a technique which alleviates at least some of these problems.

According to the present invention, there is provided a method of delivering a molecule to a lipid bilayer, the method comprising:

providing a probe capable of holding the molecule on a carrier surface thereof;

depositing the molecule on the carrier surface of the probe;

moving the probe to engage the carrier surface against the lipid bilayer.

This method of delivering a molecule, for example a membrane protein, to a lipid bilayer produces a number of advantages over the known technique described above of simply putting the membrane protein into solution and waiting. The main advantages are that the method is quick and simple to carry out. The steps of putting the molecule on the probe and moving the probe to engage against the lipid bilayer are very simple to perform experimentally and do not require great skill and expertise. The probe is a macroscopic element which allows it to be manipulated manually or by a mechanical system such as a micro-manipulator. These steps may also be performed very quickly.

When applied to a molecule which is a membrane protein, the step of moving the probe to engage the carrier surface against the lipid bilayer causes the membrane protein to be inserted into the lipid bilayer. In practice, the insertion occurs very quickly after engagement of the carrier surface against the lipid bilayer. Typically the insertion occurs within a few seconds of the engagement. This speed is very significant in practical terms as it allows repeated performance of an experiment at a rate which is many times greater than that achievable by adding the membrane protein to the solution and waiting for insertion into the bilayer. Relative to that known technique, the present invention provides the capability of very high throughput experimentation. Furthermore, the speed may be achieved with a much lower skill level on the part of the user. For example, the method may be applied to provide high through-put screening of different membrane proteins and/or analytes, for example screening of different membrane proteins and/or analytes. Examples where the high speed of the invention would be particularly useful include, inter alia: (1) functional investigation of channels, pores or other membrane proteins and (2) determination of the function or activity of a membrane protein in the presence of an analyte, which may provide for identification of either or both of the membrane protein and the analyte.

Further advantages of the present method are as follows.

The ease and speed of performance provide the method with the capability of facilitating the generation of arrays of membrane proteins e.g. to act as a sensor array for high throughput screening. This might be achieved either by insertion of respective proteins in separate lipid bilayers or by sequential insertion of multiple proteins in a single bilayer. The proteins may be of the same or different type. In particular, the method could readily be automated for use in preparing such arrays. Such arrays of membrane proteins especially engineered proteins with different structures have to date been difficult to implement but are expected to be very useful, for example as tools allowing the recognition of a particular analyte of interest or for recognition of complex mixtures of analytes. For example a range of compounds could be added to the sensor array and the changing function monitored.

The direct nature of the method may allow the investigation of membrane proteins which have previously been difficult to reconstitute in artificial lipid bilayers.

The high speed of the method means that it may be applied to lipid bilayers of relatively small area, which in turn allows reduction of the electrical noise and improvement in the stability of the lipid bilayer.

A number of advantages derive from the use of a probe in itself. One advantage is to simplify preparation of the molecule to be delivered. For example, the molecule may be obtained from media other than aqueous solution. One option is for the probe to be rubbed over a sample. The sample may be for example a cell culture, a bacterial colony or a fungal system. In these cases the sample may be unlysed. Also, the sample may be non-cellular, for example a "synthetic" ribosomal system.

This allows the proteins to be easily transferred to the lipid bilayer for study without requiring complicated extraction and purification techniques for the proteins, such as IVVT and plasmid preparation, or DNA amplification and protein assembly and purification. Furthermore, the bacterial colony is an ideal storage system for proteins. Since there are no additional processes between protein expression in bacteria and delivery to the bilayer, the exposure of more delicate proteins to potentially denaturing conditions is minimised. Alternatively, another possible advantage is that the probes may be capable of storage after deposition of the molecules on the carrier surface, under proper conditions for example low temperatures and appropriate humidity.

Prior techniques for delivering molecules to a lipid bilayer tend to avoid engagement with a macroscopic object, presumably because of an expectation that the lipid bilayer would not withstand the mechanical impact of the engagement. However, it has been appreciated by the present inventors that in fact it is possible for a probe to engage the lipid bilayer without causing rupture or damage. In experiments described in more detail below, it has been demonstrated that the method is in fact very robust. The lipid bilayer was capable of being engaged by moving the probe manually without the need for any special measures to control the applied force (although such control or even automation is feasible and within the scope of the invention).

Contrary to the probe damaging the lipid bilayer, in the case of a probe having a carrier surface with an area which is greater than the area of the lipid bilayer, it has been found that the probe actually enhances the mechanical stability of the lipid bilayer whilst in engagement. In general, very little pressure is needed to hydrostatically burst a lipid bilayer. There are types of experiment which subject the lipid bilayer to hydrostatic pressure, for example in microfluidic applications where pressure driven chemical delivery is of paramount importance, or in other experiments where there is a flow of fluid past the lipid bilayer. In such types of experiment the probe may be used to support the lipid bilayer and reduce the risk of rupture.

As already mentioned, the present method has particular application to insertion of a membrane protein, as the molecule, into a lipid bilayer. In this case, the method may be applied to a stochastic sensing technique, for example in which the molecule is a membrane protein which is a pore or a channel and the apparatus further comprises an electrical circuit capable of measuring an electrical signal across the lipid bilayer The method is applicable to any type of membrane protein. This has been demonstrated for integral membrane proteins, but is equally expected for peripheral membrane proteins. The present method applies to any membrane proteins including the two major classes of a $\beta$-barrel or an $\alpha$-helical bundle. An important application is a membrane protein which is a pore or a channel. Besides a protein pore or channel, further possible membrane proteins include, but not exclusively, a receptor, a transporter or a protein which effects cell recognition or a cell-to-cell interaction. As already mentioned, a lipid bilayer into which a membrane protein has been inserted in accordance with the method of the invention may be used in a stochastic sensing technique. The lipid bilayer may also be used to study the properties of the membrane protein inserted therein. For example, the voltage dependence of the properties of the membrane protein may be determined. Techniques for studying membrane proteins in lipid bilayers are well known in the art. The function of a channel or pore may be determined by measuring, for example, an ionic current flowing across the lipid bilayer in a similar manner to the stochastic sensing technique. The function of a transporter may be determined by measuring the amount of a molecule translocated across the lipid bilayer, for example by mass spectrometer or ELISA or by using a substrate which is tagged fluorescently or radioactively.

As well as molecules which are membrane proteins, it is expected that the present invention will be applicable to other types of molecule which it is desired to deliver to a lipid bilayer. One example is that the molecule is an analyte which is to be delivered to a lipid bilayer which already has a membrane protein inserted therein so as to perform analysis of the analyte. A further good example is an analyte which is scarce such as unamplified DNA. This embodiment is useful for studying the analyte dependence of a membrane protein. The analyte may be a ligand for the membrane protein present in the lipid bilayer, for example a receptor or a ligand-gated pore channel. In this case the movement of the probe to engage to the carrier surface allows the analyte to interact with the membrane protein. The method of the invention may therefore be used to provide a receptor or ligand-gated pore or channel with its ligand.

It is also expected that the probe may be used to capture molecules which have translocated through or have been transported across a lipid bilayer having a membrane protein inserted therein, for example by diffusive transport through a protein pore or by membrane protein-mediated transport across lipid bilayers. With such transport using a single membrane protein, with conventional techniques the time required to reach an amount of translocated molecule in solution which is capable of being detected is well beyond the expected lifetime of a lipid bilayer. However, by using a probe to capture translocated molecules, it is expected that a sufficient amount of the transported molecule could be captured much sooner. The probe could subsequently be removed and taken elsewhere for analysis (for example by mass spectrometer or ELISA).

Where different molecules are being delivered and/or captured it is possible to use an apparatus having plural probes, for example one in respect of each molecule being delivered or captured. The probes might be arranged on the same side, or opposite sides, of the lipid bilayer as convenient.

The lipid bilayer may be a bilayer of any membrane lipid, including a phospholipid, a glycolipid or cholesterol and including mixtures. The present method is of particular application to technologies using a planar lipid bilayer, for example in an apparatus comprising a chamber body defining a chamber, a wall of the chamber having an aperture in which the lipid bilayer is formed, the chamber containing an aqueous solution. Therefore, according to a further aspect of the present invention, there is provided an apparatus for performing stochastic sensing with a membrane protein, the apparatus comprising:

a chamber body defining a chamber capable of containing an aqueous solution, a wall of the chamber having an aperture capable of supporting a lipid bilayer across the aperture;

a probe capable of holding the molecule on a carrier surface thereof, the probe being movably mounted on the chamber body to allow movement of the carrier surface against the aperture for engagement of the carrier surface against a lipid bilayer supported across the aperture.

The method is expected to be equally applicable to other types of lipid bilayer including but not exclusively a membrane of a cell, a membrane of an organelle or a liposome. Insertion of a membrane protein into intact cells allows the membrane protein to be studied under conditions similar to its native environment. For example, the functioning of a pore, channel or transporter may be studied in the presence of a normal intracellular environment. Receptors inserted into the membrane of intact cells may also be studied in the presence of their associated proteins, for example G-proteins and other second messenger system components.

The carrier surface is capable of holding the molecule. As the molecule is held on the surface, this allows it to interact with the lipid bilayer, for example in the case of a molecule which is a membrane protein by insertion of the lipid bilayer into the lipid bilayer. In general, the carrier surface may be any type of surface which allows the molecule in question to be held for delivery to the lipid bilayer. Some examples are as follows.

Preferably, the probe is capable of holding the molecule by adsorbing the molecule on said carrier surface. One option which allows adsorption to occur is that the probe comprises a body having a drop of gel, such as a hydrogel, protruding from the body, the gel being capable of holding the molecule on a protruding surface thereof which protruding surface constitutes said carrier surface. However, the use of a gel is not essential. For example, the carrier surface may alternatively be the surface of a fluid or a solid which adsorbs the molecule. Suitable solids include polymers or glasses, either of which may be selected to have suitable properties to assist the adsorption of the molecule.

Furthermore, the molecule may be held by other types of physical or chemical bond. For example, the carrier surface may be chosen to specifically bind to the molecule in question.

The carrier surface may also be treated to achieve suitable surface properties, for example by coating or by chemical modification. This ability to adapt the chemistry of the carrier surface is a particular advantage of a carrier surface made of a solid. One type of coating which may be applied is polyethylene imine, or any polyelectrolyte which increases or decreases the affinity for a membrane protein or other molecule of interest. One type of chemical modification which may be applied is a silane modification.

In one type of method, the carrier surface is capable of holding the membrane protein less strongly than the lipid bilayer, and the method further comprises, after said step of moving the probe to engage the carrier surface of the probe with the lipid bilayer, moving the probe to disengage the carrier surface of the probe against the lipid bilayer, thereby leaving the inserted the membrane protein in the lipid bilayer.

With this type of method the membrane protein is released from the carrier surface of the probe. This may be desirable in some practical situations, because it allows the probe to be removed without interfering with the procedure.

However, such removal of the probe is not essential. As an alternative, the probe may remain engaged with the lipid bilayer during performance of an experimental technique. This is acceptable provided that the probe does not interfere with the experiment. For example, in the case of a stochastic sensing, this may be achieved by use of a probe in which the carrier surface is the surface of a material through which the aqueous solution may diffuse, for example a hydrogel. This allows flow of the ionic current to the membrane protein even while remaining held on the probe.

In one type of embodiment, the carrier surface has an area which is greater than the area of the lipid bilayer, advantageously by at least an order of magnitude. In this case, the probe preferably uses the surface of a drop of gel as the carrier surface. This provides the advantage of reducing the pressure on the lipid bilayer because the applied force is spread over the entire area of the carrier surface. This provides for easy engagement of the probe with the lipid bilayer as the probe may simply be moved against the lipid bilayer until the movement is resisted by the element supporting the lipid bilayer. The reduced pressure also assists in preventing the probe from damaging the lipid bilayer. In addition, the use of a relatively large probe assists in aiming it at the lipid bilayer during the movement of the probe, as well as having the capability of enhancing the mechanical stability of the lipid bilayer as discussed above.

In another type of embodiment, the carrier surface is smaller than the lipid bilayer. In this case, the carrier surface is typically the surface of a solid. The nature of the solid is not critical provided the probe is capable of holding the molecule as described above. One possible solid is glass, although experiments have successfully been carried out even with the needle of a cactus plant. This type of probe provides a number of advantages as follows. As a result of the carrier surface being smaller than the lipid bilayer, contact with the lipid bilayer can be guaranteed, although there is a corresponding disadvantage as compared to a probe having a carrier surface of large area that careful control of the movement of the probe is needed to bring it to the correct position for engagement with the lipid bilayer. The small probe also causes a lesser amount of the molecules in question to be delivered to the lipid bilayer which has advantages in many cases, for example by requiring a lesser amount of the molecules.

To allow better understanding, an embodiment of the present invention will now be described by way of non-limitative example with reference to the accompanying drawings, in which.

Figure 1:
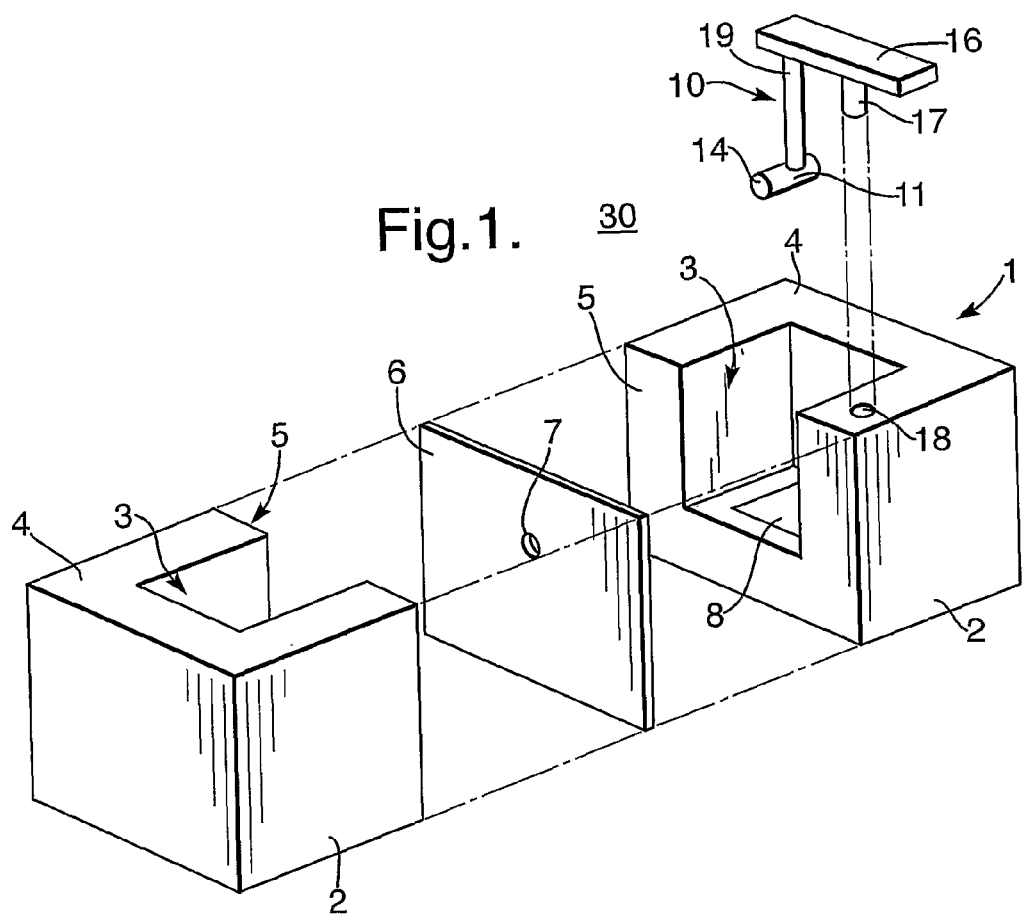
FIG. 1 is an exploded view of a first apparatus for performing stochastic sensing.

A first apparatus 30 which may be used to perform the present method is illustrated in FIG. 1. The first apparatus 30 includes an electrophysiology cell 1 which is of a conventional type and construction for the performance of stochastic sensing using a membrane protein inserted in a lipid bilayer.

The electrophysiology cell 1 comprises two chamber body portions 2 having constructions which are mirror images of each other. The chamber body portions 2 may be made from Delrin (trademark). The chamber body portions 2 each define a chamber portion 3 having an opening in the upper surface 4 of the respective chamber body portion 2. The chamber portions 3 each have a volume of a few millilitres, for example 1.5 ml. The chamber portions 3 have no wall on a side surface 5 of the respective chamber body portion 2. To form a chamber body, the two chamber body portions 2 are assembled together with their side surfaces 5 facing one another so that the respective chamber portions 3 are aligned and together form a chamber. The chamber body portions 2 may be attached by any suitable means, typically a clamp or an adhesive.

The electrophysiology cell 1 further comprises a septum 6 made of polycarbonate or any other suitable polymer. Each face of the septum 6 may be coated in a conventional manner, for example with 10% (V/V) hexadecane in pentane. The septum 6 is positioned between the facing side surfaces 5 of the two chamber body portions 2, for example by adhering both chamber body portions 2 to the septum 6. Accordingly, the septum 6 forms a wall which divides the chamber formed by the two chamber portions 3.

Figure 3:
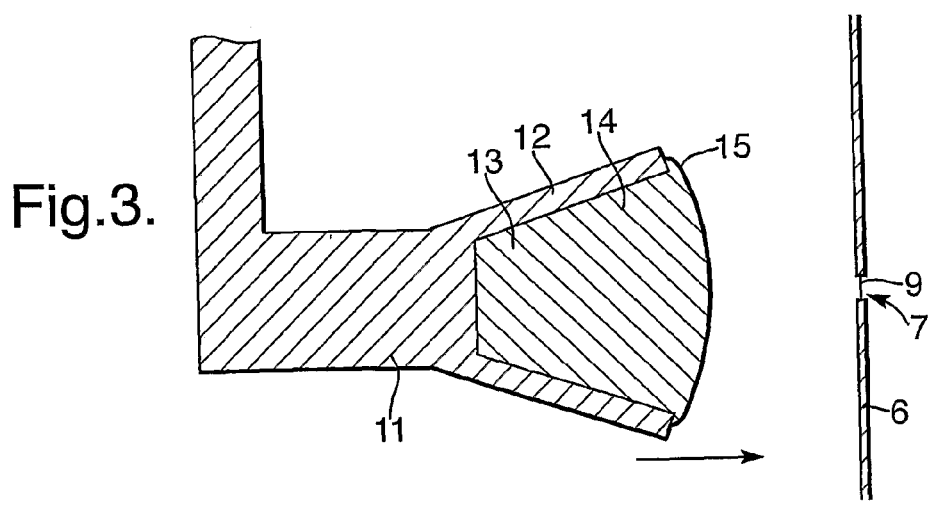
FIG. 3 is a cross-sectional view of the carrier portion of the probe of the first apparatus of FIG. 1.

The septum 6 has an aperture 7 which is aligned with the chamber portions 3 when the electrophysiology cell is assembled. In use, a lipid bilayer 9 is formed across the aperture 7 as shown in FIG. 3. The septum 6 is sufficiently thin to facilitate formation of the lipid bilayer 9, for example being 25 μm thick. The aperture 7 may in general be of any shape or size which is capable of supporting the lipid bilayer 9, but might preferably be circular with a diameter of around 100 μm.

Figure 2:
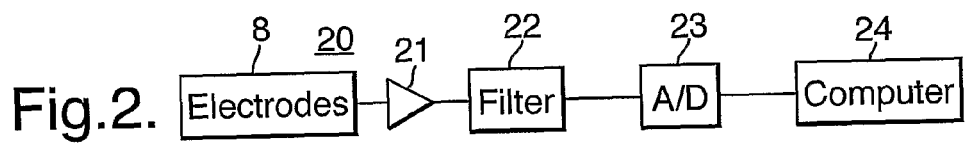
FIG. 2 is a schematic diagram of the electrical circuit of the first apparatus of FIG. 1.

The electrophysiology cell 1 further includes respective electrodes 8 provided in each chamber portion 3 of each one of the chamber body portions 2. The electrodes 8 may be Ag/AgCl electrodes. The electrodes 8 form part of an electrical circuit 20 which is capable of measuring an electrical signal across a lipid bilayer 9. The electrical circuit 20 is illustrated schematically in FIG. 2 and is of a conventional type for performing stochastic sensing by detecting the current flowing across the lipid bilayer 9.

The electrodes 8 are connected to an amplifier 21 such as a patch-clamp amplifier (e.g. an Axopatch 200B supplied by Axon Instruments) which amplifies the current signal output from the electrodes 8.

The current signal output by the amplifier 21 is supplied through a low-pass filter 22, such as a Bessel filter (e.g. with characteristics 80 dB/decade with a corner frequency of 2 kHz).

The current signal output by the low-pass filter 22 is supplied to an A/D convertor 23, such as a Digitata 1320 A/D converter supplied by Akon Instruments. The A/D convertor 23 might typically operate with a sampling frequency of 5 kHz. The A/D convertor 23 converts the current signal into a digital signal which is then supplied to a computer 24 for analysis. The computer 24 may be a conventional personal computer running an appropriate program to store the current signal and display it on a display device.

The electrophysiology cell 1 may be used to form the lipid bilayer 9 in a conventional manner. A typical experimental technique to form the lipid bilayer 9 is as follows.

After assembly of the electrophysiology cell 1, both chamber portions 3 are filled with an appropriate buffer solution which is chosen having regard to the membrane protein which is being inserted into the lipid bilayer 9.

Then, a solution of a desired membrane lipid is added into the buffer solution in each chamber portion 3. In general, any membrane lipid may be used including a phospholipid, a glycolipid or cholesterol. A typical example used in the experiments reported below is diphytanoylphosphocholine which may be dissolved in pentane, for which a typical amount might be a volume of 8 μl of the solution at a concentration of 10 mg/ml. Subsequently the solvent, for example pentane, is allowed to evaporate to form a monolayer of the membrane lipid on the surface of the buffer solution.

To form the lipid bilayer 9, the liquid level in each chamber portion 3 is lowered below the aperture 7 and subsequently raised above the aperture 7. Such formation of a lipid bilayer 9 can be repeated to perform new experiments.

After insertion of the membrane protein into the lipid bilayer 9 (using the technique described in detail below), an electrical signal developed across the lipid bilayer 9 is monitored by the electrical circuit 20 in a conventional manner.

There will now be described the modifications to the conventional electrophysiology cell 1 which allow the present method to be performed.

The first apparatus 30 of FIG. 1 further comprises a probe 10 which may be mounted on the electrophysiology cell 1 and is a macroscopic element. This allows the probe 10 to be manipulated manually.

The probe 10 has a carrier body 11 which is shown in cross-section in FIG. 3. The carrier portion 11 has at a distal end thereof a cupped portion 12 which defines a recess 13. A drop of gel 14 is deposited in the recess 13. The gel is a hydrogel, for example agarose gel or a synthetic gel such as polyacrylamide. For example, in the experiments reported below, the gel 14 was 5% low melt agarose gel. The gel 14 protrudes from the carrier portion 11 so that the protruding surface 15 of the gel 14 is gently curved. The cupped portion 12 is circular in this embodiment but may in general have any shape.

The area of the protruding surface 15 of the gel 14, which is principally controlled by the area of the opening of the recess 13 in the cupped portion 12, is preferably at least 1 mm², more preferably at least 10 mm². For example, the cupped portion 12 might typically have a diameter of around 3 mm. Thus, the area of the protruding surface 15 of the gel 14 is greater than the area of the aperture 7 by at least an order of magnitude or more preferably by at least two orders of magnitude.

The carrier body 11 is supported in the chamber portion 3 of one of the chamber body portions 2 with the protruding surface 15 of the gel 14 facing the aperture 7 across which the lipid bilayer 9 is formed. To provide such support, the probe 10 comprises a boom 16. A stub axle 17 protrudes from the boom 16. The stub axle 17 fits in a hole 18 formed in the upper surface 4 of one of the chamber body portions 2. The stub axle 17 and hole 18 act as a pivotal mounting for the boom 16 allowing the boom 16 to be rotated over the upper surface 4 of the chamber body portion 2. The carrier body 11 is supported from the boom 16 with the protruding surface 15 of the gel 14 aligned with the aperture 7 by an arm 19 which extends from the carrier body 11 out of the chamber portion 3 through the opening in the upper surface 4 to the boom 16. Accordingly, manual manipulation of the boom 16 about the pivot formed by the stub axle 17 and the hole 18 causes movement of the carrier body 11 towards and away from the aperture 7 and the lipid bilayer 9.

The method of using the first apparatus 30 will now be described.

The protruding surface 15 of the gel 14 is used as a carrier surface to carry a molecule and deliver it to the lipid bilayer 9. There will first be described the case that the molecule is a membrane protein which is delivered to the lipid bilayer 9 for insertion therein.

As a preliminary step, the protruding surface 15 of the gel 14 is surface dried and partly dehydrated by holding it briefly under a stream of nitrogen. The membrane protein is then deposited onto the protruding surface 15 of the gel 14. This may be achieved by simply dropping a solution of the membrane protein using a pipette. The solution may be an in vitro transcription/translation mix. Equally the deposition may be carried out in any other way, for example by rubbing the gel 14 over a sample such as a cell culture or, a bacterial colony. In such cases, the process of extracting a viable membrane protein is considerably shortened and simplified by slipping purification steps completely.

When the membrane protein is deposited in solution, the solvent is absorbed into the gel 14. Deposition of the membrane protein causes the membrane protein to be adsorbed onto the protruding surface 15 of the gel 14. Thus, the membrane protein is held on the protruding surface 15 which acts as a carrier surface for the membrane protein.

After deposition of the membrane protein, the probe 10 is mounted on the electrophysiology cell 1. Then the lipid bilayer 9 is formed across the aperture 7 using the conventional technique described above.

Next, the probe 10 is moved to engage the protruding surface 15 of the gel 14 against the lipid bilayer 9 extending across the aperture 7 as shown by the arrow in FIG. 3. This movement of the probe 10 is performed simply by manual manipulation of the boom 16.

Engagement of the protruding surface 15 of the gel 14 against the lipid bilayer 9 in the aperture 7 causes the membrane protein supported on that protruding surface 15 to be inserted into the lipid bilayer 9. Such insertion typically takes a few seconds. The insertion may be monitored by observation of the electrical signal measured by the electrical circuit 20, for example by monitoring a representation of the current signal on the display of the computer 24. In the case that the membrane protein is a protein channel, a characteristic increase in the detected current is observed.

For example, FIGS. 6A to 6D show graphs of typical electrical current signals outputs during insertion of a membrane protein which is a pore into the lipid bilayer 9. In each of the graphs of FIGS. 6A to 6D, the first arrow indicates the point of time in which engagement of the protruding surface 15 of the gel 14 against the lipid bilayer 9 occurs. In each case this is followed within a few seconds by a sharp increase in the current, from 0 pA to the current of magnitude 50 pA under an applied voltage of minus 50 mV. The graphs were produced with the electrophysiology cell 1 in a metal box (not shown) to reduce ambient noise. However, during the movement of the probe 10, the box was open, so the initial current signal is very noisy. After insertion of the membrane protein into the lipid bilayer 9 the box was closed causing a large pulse of noise. However, after that there is a sharp reduction in noise to a typical value as indicated by the second arrow in each of the graphs of FIGS. 6A to 6D.

After insertion of a membrane protein into the lipid bilayer 9, the probe 10 may be maintained in position with the protruding surface 15 of the gel 14 engaging the lipid bilayer 9. This is entirely acceptable provided that the probe 10 does not interfere with the experiment which is to be performed. In this case, the use of a gel 14 to provide the carrier surface of the probe 10 is particularly advantageous because the gel 14 is porous and therefore allows the aqueous solution in the chamber portion 3 to diffuse through the gel 14. This allows the flow of ionic current through the gel 14 to the membrane protein. Leaving the probe 10 engaged with the lipid bilayer 9 generally causes membrane proteins to be repeatedly inserted and is therefore advantageous for gating channels and the like, such as KcsA potassium channel, which open transiently.

As an alternative, the probe 10 may be moved away from the aperture 7 to disengage the protruding surface 15 of the gel 14 from the lipid bilayer 9. In this case, so that the membrane protein is left inserted in the lipid bilayer 9, the carrier surface of the probe 10 must hold the membrane protein less strongly than the lipid bilayer 9. This requirement is met by the use of a gel 14 to provide the carrier surface of the probe 10.

After insertion of the membrane protein into the lipid bilayer 9, the experimental process appropriate to the membrane protein in question may be performed in a conventional manner. For example, to perform stochastic sensing, the electrical signal detected by the electrical circuit 20 is monitored.

Although the protruding surface 15 of the gel 14 engages the lipid bilayer 9, the precise nature of the interaction between the protruding surface 15 and the lipid bilayer 9 is currently unknown. It is clear that the protruding surface 15 of the gel 14 is very close to the lipid bilayer 9 but it is not clear whether there is actual physical contact or whether, for example, there remains a thin layer of aqueous solution therebetween. That being said, during the engagement it is apparent that the gel 14 does touch the septum 6. Accordingly, it is thought that the gel 14, being flexible, probably conforms with and extrudes slightly into the aperture 7, perhaps slightly deforming the lipid bilayer 9.

Despite the fact that the physical nature of the mechanical probing is not fully understood, from the point of view of the insertion of membrane proteins into the lipid bilayer 9, the method is highly reproducible and reliable. This has been demonstrated experimentally. The entire method as described above is very quick to perform. The method may be performed repeatedly, for example by breaking and re-forming the lipid bilayer 9. New membrane proteins may be inserted repeatedly without the need to deposit new amounts of the membrane protein on the probe 10. Furthermore, it is notable that simply leaving the probe 10 immersed in solution in the chamber portion 3 does not cause insertion of pores into the lipid bilayer 9 even if the probe 10 is left there for several hours. Thus insertion of the membrane protein only occurs when the probe 10 is moved to engage the carrier surface against the lipid bilayer 9.

The method is also very easy to perform. The probe 10 may be moved by simple manual manipulation of the probe 10. No special measures are needed to control movement of the probe 10. Indeed the technical method is very robust and rupture of the lipid bilayer 9 occurs very rarely. In particular, no automation of the movement is necessary, although of course such automation would be possible.

Figure 4:
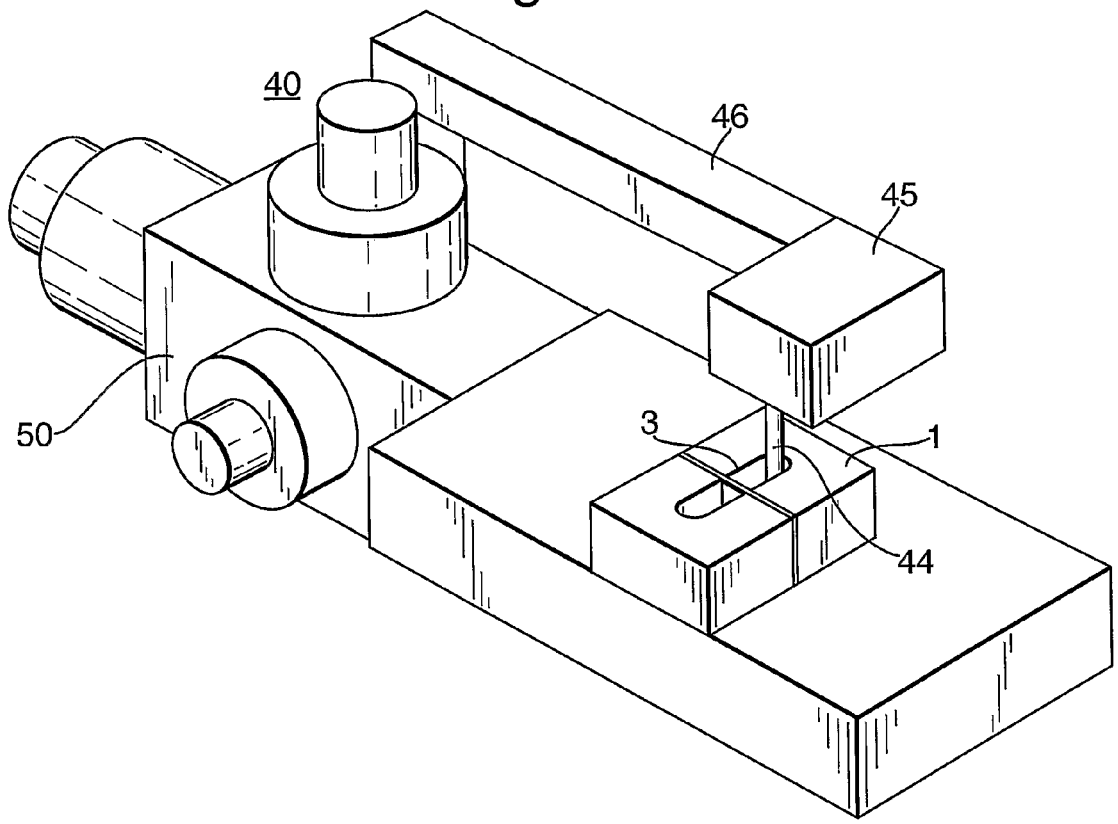
FIG. 4 is a perspective view of a second apparatus for performing stochastic sensing.
Figure 5:
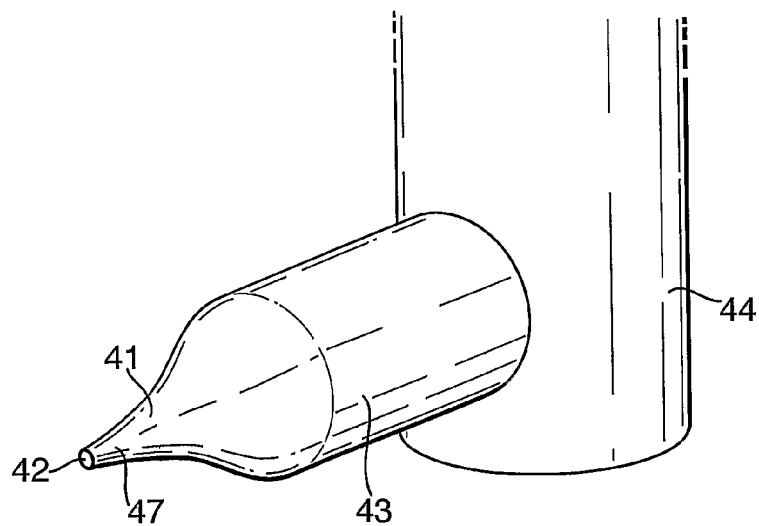
FIG. 5 is an expanded view of the probe of the second apparatus of FIG. 4.
Figure 6A:
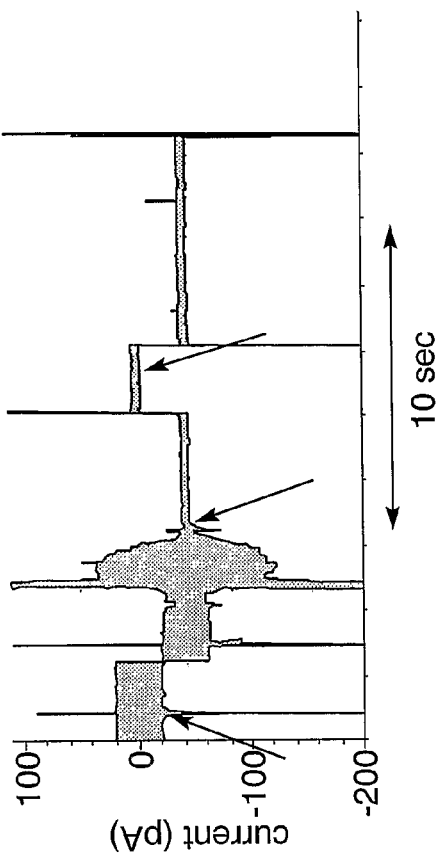
FIGS. 6A to 6D are graphs of typical electrical current signal outputs during insertion of a protein pore into a lipid bilayer.
Figure 6B:
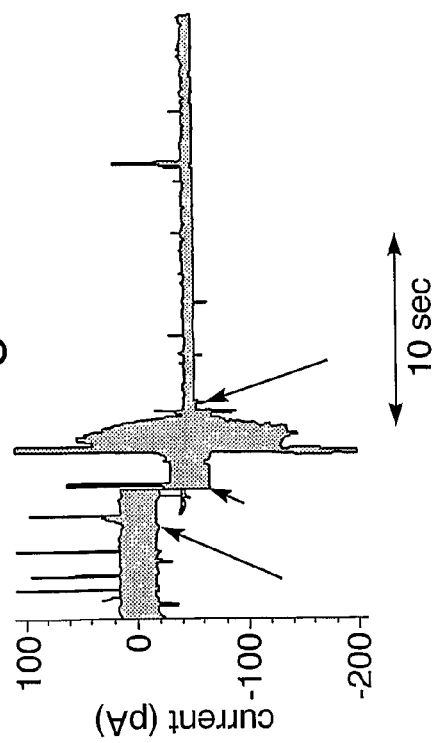
Figure 6C:
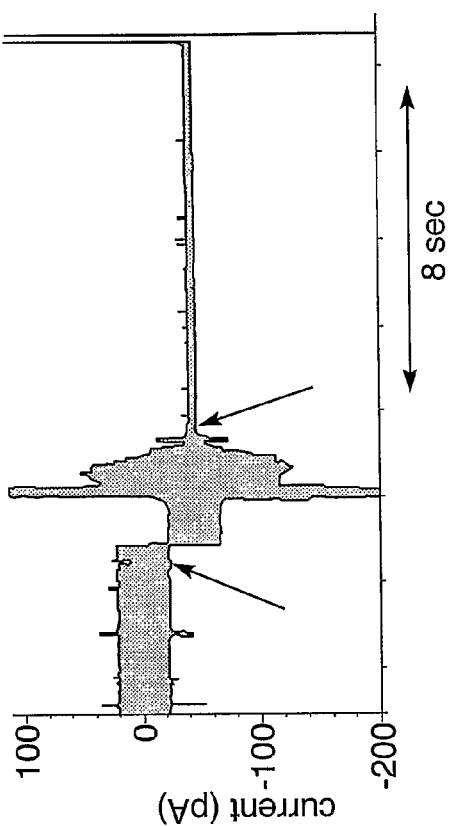
Figure 6D:
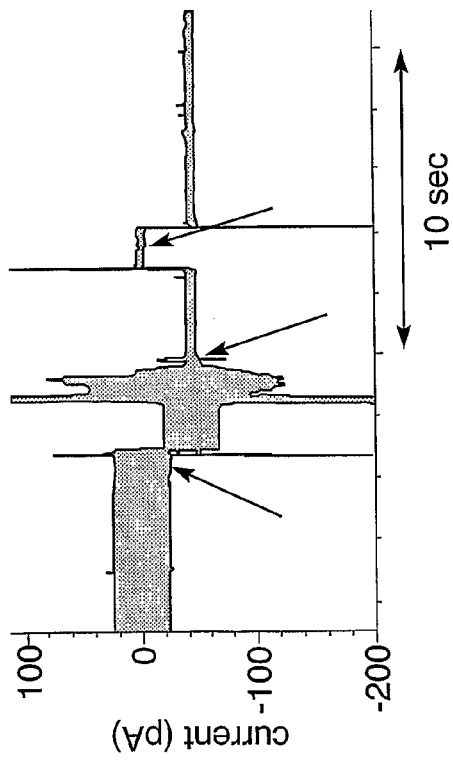

A second apparatus 40 which may be used to perform the present method is illustrated in FIG. 4. The second apparatus 40 has a fundamental difference from the first apparatus 30 in that it uses a different form of probe 41 as illustrated in FIG. 5.

The second apparatus 40 includes an electrophysiology cell 1 which is substantially identical to the electrophysiology cell 1 used in the first apparatus 30 and so for brevity a description thereof will not be repeated.

In addition, the second apparatus 40 comprises a probe 41 which takes the form of a rod of solid material having an end surface 42 which is gently rounded and contiguous with the side surfaces 47 of the probe 41. The end surface 42 and perhaps part of the side surface 47 act as a carrier surface for a molecule to be delivered to the lipid bilayer 9. The cross-section of the probe 41 at the end surface 42 is smaller than the lipid bilayer 9. This cross-section is preferably no more than 70%, more preferably no more than 50% of the area of the lipid bilayer 9. This is because the outer portion of the lipid bilayer 9 adjacent the septum 6 typically is not fully formed. Accordingly the small size of the end surface 42 of the probe 41 allows the probe to be aligned with the central portion of the lipid bilayer 9 which has the best properties for insertion of a membrane protein. Typically, the diameter of the end surface 42 of the probe 41 is in the range from 5 μm to 50 μm.

The probe 41 is formed as the tip of a rod 43 which may be a solid rod or may be a capillary. This facilitates manufacture by drawing the probe 41 using a capillary puller which is readily available commercially for example from the company Narishige. Using this puller process, the shape and sharpness of the probe 41 can be controlled by controlling the settings of the puller. After pulling the tip of the rod 43 to form the probe 41, the end surface 42 is heated to flatten out the roughness of the end surface 42. The conduit through the rod 43 is closed by the pulling process and does not have any consequence to the use of the probe 41 in the present method.

Although this manufacturing process is convenient, the manufacturing process and the nature of the resultant probe 41 are not essential. In general, it is possible to replace the probe 41 by any form of probe which has an end surface which is smaller than the lipid bilayer 9. Successful experimental results have even been achieved by replacing the probe 41 by the needle of a cactus plant which, it has been discovered, happens to be of the correct size.

The end surface 42 of the probe 41 may be treated to increase the affinity of the material of the probe 41 for the membrane protein or other molecule to be delivered to the lipid bilayer 9.

One option is to treat the end surface 42 by coating it. One possible coating is an adsorbed layer of polyethylene imine (PEI). For example, this may be achieved by a solution of PEI (e.g. at a concentration of 50% w/w) onto the end surface 42 and subsequently removing the excess PEI using a cotton wool bud. PEI advantageously increases the affinity for negatively charged membrane proteins such as αHL. Other polyelectrolytes and other materials are equally suitable.

Another possible treatment is chemical modification of the end surface 42. An example of a suitable modification is a silane modification, such as an alkyl-silane modification. An example of such a silane modification is disclosed in "Silane-modified surfaces for biomaterial immobilization", Shriver-Lake, Lisa C., Naval Research Laboratory, Center for Bio/Molecular Science and Engineering, Washington D.C., USA, Editor(s): Cass, Tonly; Ligler, Frances S. Immobilized Biomolecules in Analysis (1998), 1-14, Oxford University Press.

Accordingly, the probe 41 is a microscopic element which allows it to be manipulated by a mechanical system. In particular the probe 41 is manipulated by a micro-manipulator 50 as will now be described. The rod 43 is mounted on a column 44 suspended from a block 45 which is itself mounted on a link arm 46 of the micro-manipulator 50. The block 45 is transparent to allow the probe 41 to be seen inside the chamber portion 3 of the electrophysiology cell 1. The micro-manipulator 50 is of a conventional type, for example as supplied by the company Narishige. The micro-manipulator 50 provides controlled movement of the probe 41 in three dimensions.

The method of using the second apparatus 40 will now be described.

It is noted that the small size of the probe 41 in the second apparatus 40 requires there to be greater control over the movement of the probe 41 than is needed for the probe 10 in the first apparatus 30. The micro-manipulator 50 provides such control. In fact two types of control are necessary.

The first type of control is to align the probe 41 with the lipid bilayer 9 by moving the probe 41 parallel to the lipid bilayer 9. This alignment may be achieved by viewing the probe 41 as it moves towards the lipid bilayer 9, for example using a stereo-microscope while the electrophysiology cell 1 is illuminated under a bright light. After this alignment has been performed once, the position settings on of the micro-manipulator 50 may be fixed to maintain this alignment.

The second type of control is control of the movement of the probe 41 towards the lipid bilayer 19. The small size of the probe 41 enables it to stretch the lipid bilayer 9 by a significant amount, and perhaps even to penetrate the lipid bilayer 9 without causing rupture (although this currently remains unclear).

It is necessary to stop the movement with the end surface 42 in engagement with the lipid bilayer 9. This control of the movement of the probe 41 is carried out by performing an initial calibration step during which the capacitance of the lipid bilayer 9 is monitored. To monitor the capacitance, there is applied across the electrodes 8 and hence across the lipid bilayer 9 a voltage waveform in the shape of an oscillating ramp having a slope of constant magnitude but alternating in sign. The output current is then monitored. The magnitude output current is proportional to the slope of the ramp of the voltage signal (which is a constant) and is also proportional to the capacitance of the lipid bilayer 9. The current changes between a positive and negative current as the sign of the ramp voltage changes. As a result, the output current signal is a square wave having an amplitude proportional to the capacitance of the lipid bilayer 9. Thus the output current signal is monitored to monitor the capacitance of the lipid bilayer 9.

During the calibration step, the probe 41 is moved at a slow rate towards the lipid bilayer 9. When the probe 41 comes into engagement with the lipid bilayer 9, this causes the monitored capacitance to change. When this is detected from the output current signal, the movement of the probe 41 is stopped. At this point of engagement, at least part of the end surface 42 is in engagement with the lipid bilayer 9. The probe 41 may locally deform the lipid bilayer 9 so that in increased area of the end surface 42 and even part of the side surfaces 47 engage the lipid bilayer 9.

The position of the probe 41 is noted. Subsequently the micro-manipulator 50 may be used to return the probe 41 to the same position determined during this calibration step without the need to monitor the capacitance again.

Whilst the micro-manipulator 50 is effective to provide the necessary degree of control, such control may be achieved in other ways, for example by using mechanical stops or by driving the movement of the probe 41 using a robot controlled by a microprocessor running an appropriate program.

After the alignment of the probe 41 with the lipid bilayer 9 and the calibration step have been carried out, the probe 41 may be used to deliver a membrane protein (or other type of molecule) to the lipid bilayer 9 as follows.

Firstly, the membrane protein is deposited on the end surface 42 of the probe 41. This may be achieved simply by pushing the end surface 42 of the probe 41 into a drop of a solution of the membrane protein. This causes the membrane protein to be adsorbed onto the end surface 42 and has the advantage of requiring only a small amount of the solution. Alternatively, the deposition could be carried out in any other way, for example as described above with reference to the first apparatus 30.

After deposition of the membrane protein, the probe 41 is mounted in place in the second apparatus 40. Then, the lipid bilayer 9 is formed across the aperture 7 using the conventional technique described above.

Next, the probe 41 is moved to engage the end surface 42 of the probe 41 against the lipid bilayer 9, using the micro-manipulator 50 to achieve the correct alignment and to move the probe 41 to the correct position determined in the calibration step or as seen in a stereo-microscope.

Engagement of the end surface 42 against the lipid bilayer 9 causes the membrane protein supported on the end surface 42 to be inserted into the lipid bilayer 9. Such insertion typically takes a few seconds and may be monitored as described above with reference to the first apparatus 30.

After insertion of a membrane protein into the lipid bilayer 9, the probe 41 may be maintained in position or disengaged from the lipid bilayer 9 as described above with reference to the first apparatus 30. Subsequently, an experimental process appropriate to the membrane protein in question may be performed in a conventional manner.

By way of example, the method described above has been performed to insert a number of different membrane proteins into a lipid bilayer 9. The results of these experiments will now be described with reference to FIGS. 7 to 10 which are each a graph of the electrical current signal output with a different membrane protein inserted into lipid bilayer 9.

The following methods were performed using the first apparatus 30 of FIG. 1.

Figure 7:
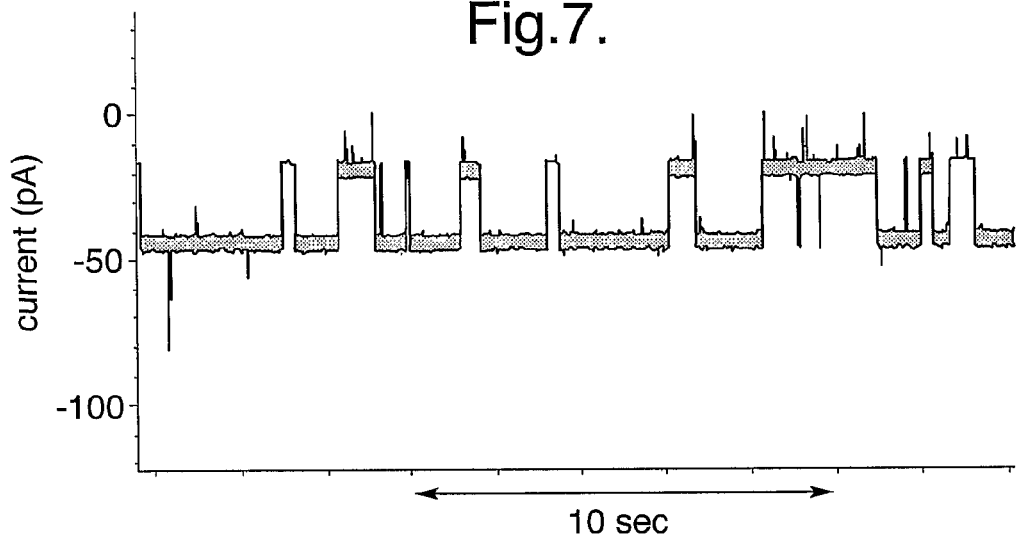
FIG. 7 is a graph of the electrical current signal output with a WT αHL protein pore inserted into a lipid bilayer.

The method was performed to insert WT (wild type) αHL protein pores which were deposited from solution onto the probe 10. The detected current signal is shown in FIG. 7 for an applied voltage of minus 50 mV. In this case, the buffer solution used in the chamber portions 3 was 1M KCl, 10 mM MOPS at pH 7.00. The form of the detected current signal and the current v. voltage relationship for the signal were indistinguishable from those obtained using the same protein pores inserted by the conventional technique of simply placing the protein pore in solution and waiting for insertion. This type of protein pore binds γ-cyclodextrin. The binding kinetics and current attenuation of γ-cyclodextrin binding (15 μM) was the same for the protein pore inserted using the present method as for pores inserted by the conventional method. On the basis of these results, it is understood that the use of the probe 10 achieves proper insertion of the membrane protein without altering the properties of the lipid bilayer 9 or the membrane protein itself.

The method has also been performed to insert WT αHL protein pores firstly from an in vitro translation/transcription mix containing rRNA, tRNA, DNA, buffer, amino acids robosomes and lipids and secondly deposited onto the probe 10 by rubbing the probe 10 over a bacterial colony. In the latter case an E. Coli bacterial colony was lysed on an agar plate by applying 0.5 μL of lysis buffer, including surfactants and other components to break the cell membranes. In both cases, results were achieved similar to that shown in FIG. 7 thereby demonstrating insertion of the WT αHL protein pores rather than any other components of the in vitro translation/transcription mix or the bacterial colony.

Figure 8:
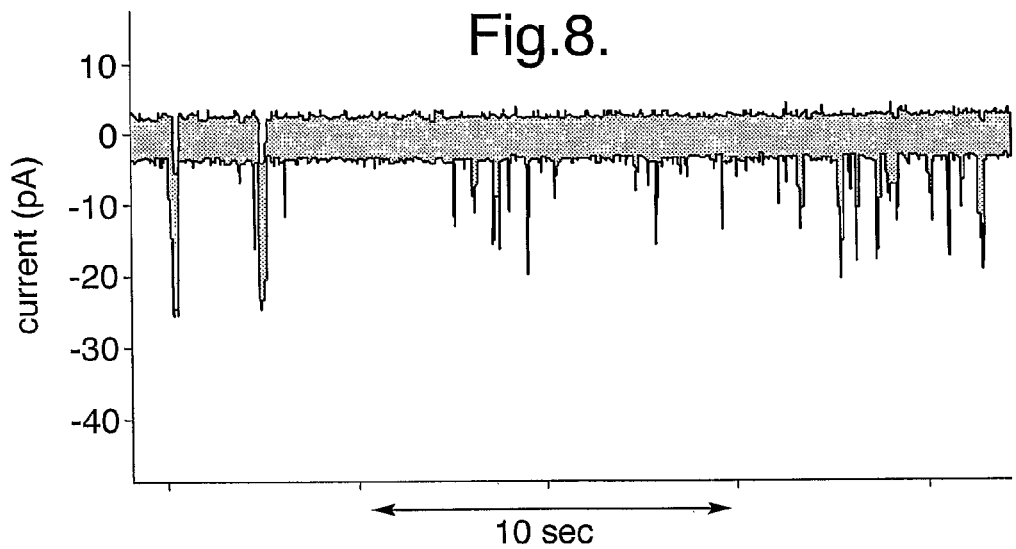
FIG. 8 is a graph of the electrical current signal output with a WT KcsA protein channel inserted into a lipid bilayer.

The method was also performed to insert a WT KcsA channel (a $K^+$ channel from *Streptomyces lividans*). In this case the solution in the chamber portions 3 was 150 mM KCl buffered with 100 mM potassium phthalate at pH 4.0. FIG. 8 shows the detected current signal with the channel gating under an applied potential of minus 150 mV. Since the opening events of these channels was rare, the probe 10 was left with the protruding surface 15 of the gel 14 engaged with the lipid bilayer 9 during the entire electrical recording in order to maximise the number of channels inserted into the lipid bilayer 9. As can be seen from FIG. 8, the detected current signal shows events which are characteristic of the opening of the channel.

Subsequently, the probe 10 was moved to disengage the protruding surface 15 of the gel 14 from the lipid bilayer 9. In this case, the same events were observed in the detected current signal. On this basis, it is understood that the engagement of the protruding surfaces 15 of the gel 14 with the lipid bilayer 9 did not interfere with the experimental process.

Figure 9:
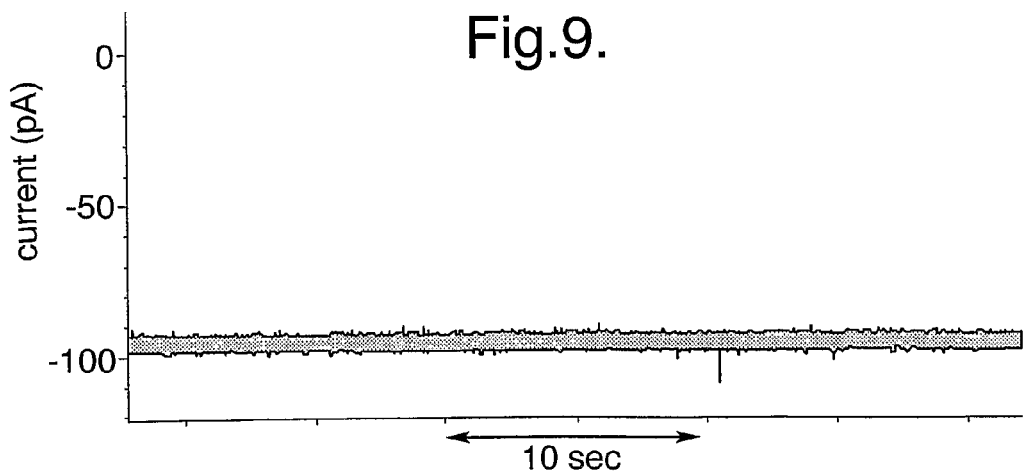
FIG. 9 is a graph of the electrical current signal output with a WT leukocidin pore inserted into a lipid bilayer.

The method was also performed to insert a leukocidin pore using a buffer solution 1M KCl, 10 mM MOPS at pH 7.00. The detected current signal after disengagement of the probe 10 is shown in FIG. 9 with an applied potential of minus 40 mV. The level of the detected current signal shows that the pore is open.

The following methods were performed using the second apparatus 40 of FIG. 4 and demonstrate the effectiveness of the method as applied to high-throughput screening.

The method was performed to insert αHL protein pores from αHL-expressing bacterial colonies disposed on an agar plate. Each time, the plate was arranged with 100 colonies of which around 95 to 99 colonies expressed WT αHL and the remainder expressed αHL mutant M113F/K147N. The number and location of the different types of colonies were not revealed to the plate screener. The method was performed in respect of each colony. The αHL protein pore was deposited on the probe by rubbing the probe over the colony.

Although the proteins were expressed in the cytoplasm of bacteria, it was not necessary to lyse or chemically treat the colonies. It is likely that enough protein was supplied by a fraction of bacteria in a colony that spontaneously lysed. Probe tips could be cleaned after screening a colony by dragging through fresh agar and the cleaned tips did not produce pores.

The protein pore was inserted into the lipid bilayer 9 and the detected current signal was monitored. After recording from a pore, it was not necessary to clean the cell 1 before moving to the next sample. Instead, the system was reset by breaking and reforming the lipid bilayer 9. These manipulations improved the speed of screening.

The probe 41 was fixed to the micro-manipulator 50, lowered into the cis chamber portion 3 of the cell 1 and engaged with the lipid bilayer 9. The probe 41 could be engaged with the lipid bilayer 9 while recording. The time needed for single or multiple pores to insert varied. The availability of protein from different colonies was not consistent. Generally, αHL colonies (WT or mutant) were potent, meaning that even a brief engagement (~0.5 sec) of the probe 41 with the lipid bilayer 9 caused multiple pores to insert. To record single pores from these colonies, the lipid bilayer 9 was broken with an electrical pulse, reformed and the probe 41 reengaged. This process was repeated until the amount of pore-forming protein on the probe 41 was reduced enough to allow the insertion of single pores. Engagement/withdrawal of the probe 41 and reformation of the lipid bilayer 9 could be repeated at least 5 times per minute. However, typically, only two to four iterations were needed to obtain single functional pores.

The detected current signal allowed the two types of αHL protein pore to be distinguished. Both types of αHL form pores of similar ionic conductance. However, only the mutant αHL binds the molecular adapter βCD from the cis side. The plate was screened by the probe method. Both cis and trans chamber portion 3 contained 10 mM MOPS, 1M KCl, pH 7.0, and the lipid bilayer 9 was held at −50 mV. Recording was performed with 90 μM βCD in the cis chamber portion 3. βCD bound to the mutant pores but not the WT pores.

Figure 10A:
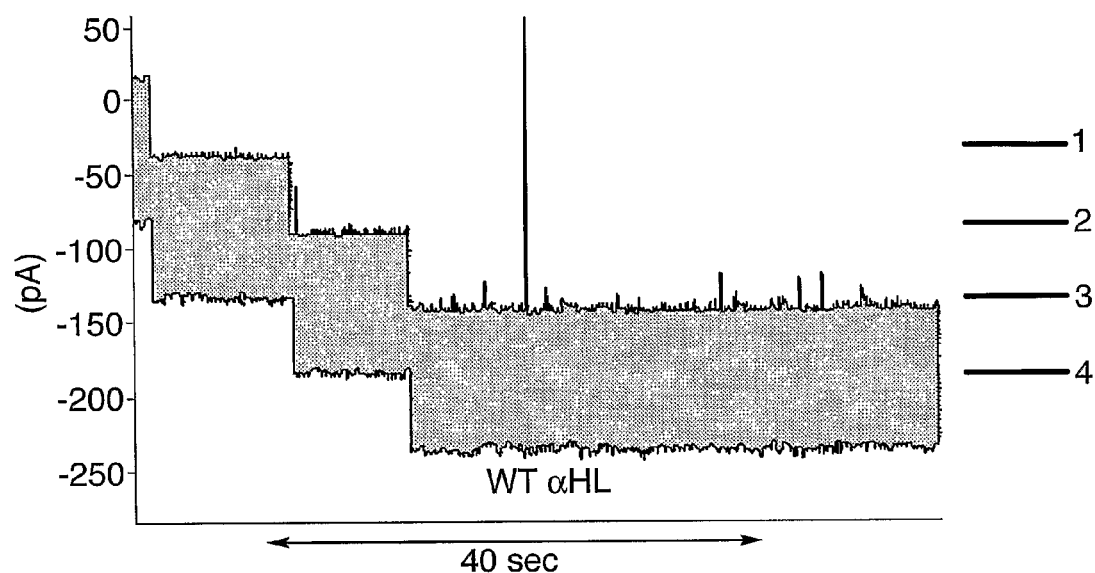
FIGS. 10A and 10B are graphs of the electrical current signal output with a WT αHL protein pore and an αHL mutant M113F/K147N protein pore, respectively, inserted into a lipid bilayer.
Figure 10B:
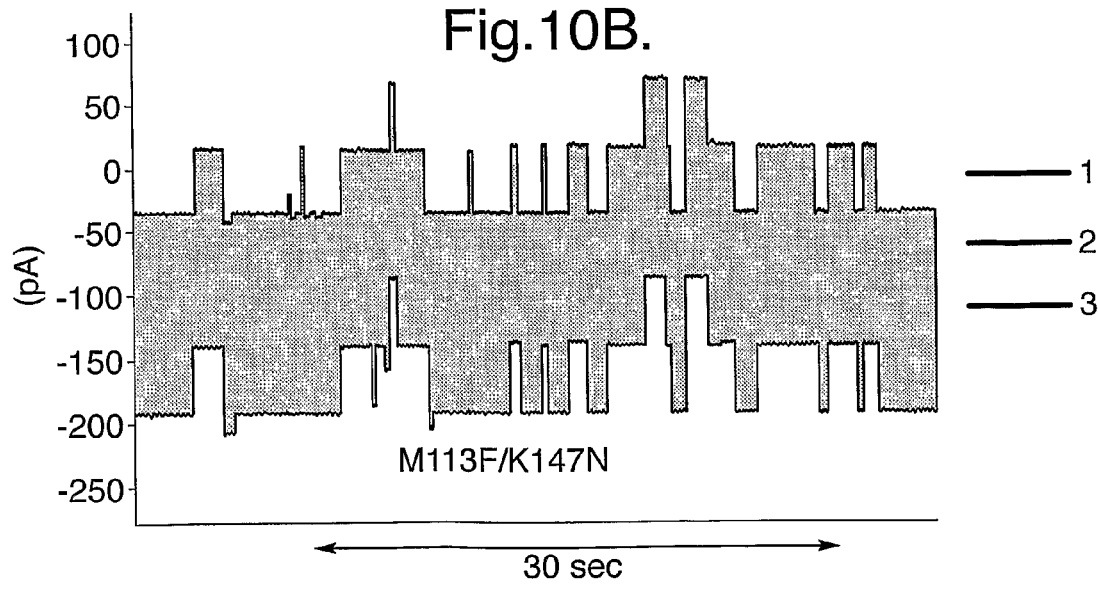

WT αHL showed a stepwise increase in current with each pore that inserted into the bilayer. An example for the case of four pores is shown in FIG. 10A. However, the M113F/K147N mutant bound the βCD, giving a characteristic attenuation of the current. An example in the case of two pores is shown in FIG. 10B. After screening all 100 colonies, the mutant-expressing colonies were found at positions that corresponded exactly to those subsequently revealed by the plate preparer.

This experiment demonstrates rapid screening for rare instances of novel function in a background of WT pores.

Next, the method was performed to deposit two protein subunits which combined to yield an active protein pore, in particular leukocidin which is composed of two different monomers, four Luk F and four Luk S subunits, arranged in alternating fashion around a central axis to give an octameric pore.

Separate *E. coli* colonies expressing WT Luk F and WT Luk S were scraped from agar plates, placed together on a fresh agar surface and mixed thoroughly with a scalpel blade but were not lysed. Remarkably, it was found that the probe 41 could be dipped into the bacterial mixture and engaged with the lipid bilayer 9 to produce WT leukocidin pores. Thus, it was possible to assemble fully functional bi-component membrane pores from separate components without purification. The insertion of single leukocidin pores usually required longer probe engagements than those used for αHL colonies, which might be expected because leukocidin has a much lower activity than αHL in hemolytic assays. Typically, using freshly mixed colonies, the probe 41 might be engaged with the lipid bilayer 9 for several seconds before a single pore inserted. However, mixed colonies often became more potent with time, some yielding as many pores per second as αHL colonies. Mixtures of leukocidin colonies could be stored for at least one month at 4° C. on agar plates and still produce protein pores by the probe method.

Previously, it has been shown that certain amino acids in the β barrel of αHL can be mutated to enhance the binding of βCD (both αHL and βCD have 7-fold axial symmetry).

For example, when the M113 residue of αHL is mutated to phenylalanine, the duration of binding of βCD is ~$3 \times 10^4$ times longer in comparison to WT αHL. The permethylated form of βCD, TRIMEB, binds to M113F αHL ~4 times longer than βCD. Based on these findings, it was hypothesized that similar modifications could be made in the β barrel of leukocidin, such that the mutant proteins would bind permethylated γCD, TRIMEG (both leukocidin and TRIMEG have 8-fold axial symmetry).

Based on sequence homology, the crystal structure of the αHL heptamer and the crystal structures of the Luk F (HlgB), Luk F (PV) and Luk S (PV) monomers, the alignment of amino acids in the β strands of the barrel was modelled for all three monomers, Mutations were made that replaced natural amino acids at various positions along the β strands of Luk F and Luk S with phenylalanine. Inside the β barrel, the mutated residues might align to form a ring of eight phenylalanines or two separated rings of four phenylalanines. By analogy with αHL M113F, it was hypothesized that the aligned phenylalanine residues would create a form of leukocidin that binds TRIMEG.

Previously, mutant leukocidins were prepared by expressing individual monomers of Luk F and Luk S by IVTT. The monomers were then assembled on rabbit red blood cell membranes to obtain octamers. The octamers were subsequently gel purified.

In contrast, in the present method, the far more rapid probe procedure was used to obtain functional leukocidin pores from mutant subunits. For each of thirty-five new combinations of the two subunits, three individual pores were examined and the kinetic data were averaged. The Luk F Q112F/Luk S S108 F combination bound TRIMEG longer than any other combination by at least two orders of magnitude, while WT leukocidin bound TRIMEG with the shortest dwell time. These data suggest that the amino acids at M113, Q112, and S108 share similar locations and orientations in αHL, Luk F and Luk S respectively.

This experiment supports the idea that the βPFT from the colonies is monomeric. In this case, the water-soluble monomers must assemble after mixing. The bacterial strains, used in these experiments must have endogenous membrane channels and pores. However, interference from these was not observed in the electrical recordings. The transfer of overexpressed proteins from bacterial colonies to planar bilayers is inefficient and it is reasonable to expect that the insertion of endogenous proteins will occur infrequently. While inefficient transfer would be undesirable in bulk assays, it is ideally suited for screening by single-channel recording.

While this massive data collection would have been laborious by alternative approaches, the application of mixed Luk colonies with the glass probe allowed efficient screening. This clearly demonstrates the effectiveness of the present method in allowing high through-out screening.

The experimental results reported above demonstrate insertion of examples from the two major classes of membrane protein, that is β-barrels (e.g. the αHL pore and the leukocidin pore) and α-helical bundles (e.g. the K$^+$ channel) can be inserted using the present method. On this basis, it is understood that any membrane protein could similarly be inserted into a planar lipid bilayer 9. The method is expected to allow delivery of any material, including cell lysates or fractions, containing insoluble membrane proteins directly from their native environment to the lipid bilayer 9.

Similarly, it is expected that the same technique could be applied to insert membrane proteins into any other lipid bilayer 9, for example a cell membrane, an organelle membrane or a liposome.

It is expected that the present method could be applied to deliver molecules other than membrane proteins to a lipid bilayer 9. One example is that the method could be applied to deliver an analyte to a lipid bilayer 9 in which a membrane protein is already inserted. This would have the advantage of increasing the local concentration of the analyte adjacent to the membrane protein. It would also improve the ability to analyse analytes which are relatively insoluble in an aqueous solution.

The invention claimed is:
1. A method of inserting a membrane protein into a planar lipid bilayer in an apparatus having an electrical circuit capable of measuring an electrical signal across the planar lipid bilayer, the method comprising:

providing a probe which is a macroscopic element arranged to be movable manually or by a mechanical system and having a carrier surface capable of holding the membrane protein;

depositing the membrane protein on the carrier surface of the probe so that the membrane protein is held on the carrier surface;

moving the probe manually or by a mechanical system to engage the carrier surface against the planar lipid bilayer wherein the carrier surface is capable of holding the membrane protein less strongly than the planar lipid bilayer and to cause the membrane protein to be inserted into the lipid bilayer, the insertion being detected on the basis of the electrical signal measured by the electrical circuit.

2. A method according to claim 1, wherein the method further comprises, after said step of moving the probe to engage the carrier surface of the probe with the planar lipid bilayer, moving the probe to disengage the carrier surface of the probe against the planar lipid bilayer, thereby leaving the inserted membrane protein in the planar lipid bilayer.

3. A method according to claim 1, wherein the probe is capable of holding the membrane protein by adsorbing the membrane protein on said carrier surface.

4. A method according to claim 1, wherein the probe comprises a body having a drop of gel protruding from the body, the gel being capable of holding the membrane protein on a protruding surface thereof which protruding surface constitutes said carrier surface.

5. A method according to claim 4, wherein the gel is a hydrogel.

6. A method according to claim 5, wherein the gel is either agarose gel or a synthetic gel.

7. A method according to claim 6, wherein the gel is polyacrylamide.

8. A method according to claim 4, wherein the body has a recess and the drop of gel is in the recess.

9. A method according to claim 1, wherein the carrier surface is the surface of a material through which an aqueous solution may diffuse.

10. A method according to claim 1, wherein said carrier surface is a surface of a solid.

11. A method according to claim 10, wherein the carrier surface is treated to increase the affinity for the membrane protein.

12. A method according to claim 11, wherein the carrier surface is treated by a silane modification.

13. A method according to claim 10, wherein the carrier surface has a coating of material.

14. A method according to claim 10, wherein said solid is glass.

15. A method according to claim 1, wherein said carrier surface has an area which is greater than the area of the planar lipid bilayer.

16. A method according to claim 15, wherein said carrier surface has an area which is greater than the area of the planar lipid bilayer by at least an order of magnitude.

17. A method according to claim 1, wherein said carrier surface has an area which is at least 1 mm$^2$.

18. A method according to claim 1, wherein said carrier surface is smaller than the planar lipid bilayer.

19. A method according to claim 18, wherein said carrier surface has an area which is at most 70% of the area of the planar lipid bilayer.

20. A method according to claim 1, wherein said step of depositing the membrane protein on the carrier surface of the probe comprises depositing a solution containing the membrane protein on the carrier surface of the probe.

21. A method according to claim 1, wherein said step of depositing the membrane protein on the carrier surface of the probe comprises rubbing the carrier surface of the probe over a sample containing the membrane protein.

22. A method according to claim 1, wherein the membrane protein is a pore or a channel.

23. A method according to claim 22, wherein the membrane protein is a β-barrel or an α-helical bundle.

24. A method according to claim 1, wherein the planar lipid bilayer is formed in an apparatus comprising a chamber body defining a chamber, a wall of the chamber having an aperture in which the planar lipid bilayer is formed, the chamber containing an aqueous solution.

25. A method according to claim 24, wherein the molecule is a membrane protein which is a pore or a channel.

26. A method according to claim 24, wherein the probe is mounted on the chamber body to allow movement of the probe to engage the carrier surface against the planar lipid bilayer.

27. A method according to claim 24, wherein the chamber has an opening in the upper surface of the chamber, the wall having an aperture being formed in a side surface of the chamber, and the probe comprises:

a body having said carrier surface, and an arm supporting the body in said chamber and extending out of the chamber through said opening to allow manipulation of the probe.

28. A method according to claim 27, wherein the probe further comprises a boom mounted on the chamber body and supporting the arm.

29. A method according to claim 26, wherein the probe is pivotally mounted on the chamber body.

30. A method according to claim 22, wherein the insertion of the membrane protein into the planar lipid bilayer is detected on the basis of a characteristic increase in the electrical current flowing across the planar lipid bilayer measured by the electrical circuit.

* * * * *